(12) United States Patent
Pandya

(10) Patent No.: US 10,434,014 B2
(45) Date of Patent: Oct. 8, 2019

(54) TREATMENT SYSTEM

(71) Applicant: HaloStim, LLC, Savannah, GA (US)

(72) Inventor: Andrew Pandya, Savannah, GA (US)

(73) Assignee: HaloStim, LLC, Savannah, GA (US)

( * ) Notice: Subject to any disclaimer, the term of this patent is extended or adjusted under 35 U.S.C. 154(b) by 0 days.

(21) Appl. No.: 15/785,229

(22) Filed: Oct. 16, 2017

(65) Prior Publication Data

US 2018/0271711 A1 Sep. 27, 2018

Related U.S. Application Data

(63) Continuation-in-part of application No. 15/465,416, filed on Mar. 21, 2017.

(51) Int. Cl.
| | |
|---|---|
| *A61N 1/00* | (2006.01) |
| *A61F 13/02* | (2006.01) |
| *A61F 13/00* | (2006.01) |
| *A61N 1/36* | (2006.01) |
| *A61N 1/04* | (2006.01) |

(52) U.S. Cl.
CPC .... *A61F 13/0233* (2013.01); *A61F 13/00063* (2013.01); *A61F 13/0259* (2013.01); *A61N 1/0492* (2013.01); *A61N 1/36021* (2013.01); *A61F 13/00* (2013.01); *A61F 13/023* (2013.01); *A61F 13/024* (2013.01); *A61F 13/025* (2013.01); *A61F 13/0236* (2013.01); *A61F 13/0246* (2013.01); *A61F 13/0263* (2013.01); *A61F 13/0266* (2013.01)

(58) Field of Classification Search
CPC ............ A61F 13/0233; A61F 13/00063; A61F 13/0259; A61N 1/0492; A61N 1/36021
See application file for complete search history.

(56) References Cited

U.S. PATENT DOCUMENTS

| | | | |
|---|---|---|---|
| 6,071,267 A | * | 6/2000 | Zamierowski ...... A61F 13/0203 604/289 |
| 2004/0138602 A1 | | 7/2004 | Rossen |
| 2009/0127935 A1 | | 9/2009 | Zanella et al. |
| 2013/0325097 A1 | | 12/2013 | Loest |
| 2014/0358058 A1 | | 12/2014 | Nelson |
| 2016/0081580 A1 | | 3/2016 | Bergelin et al. |
| 2016/0213521 A1 | | 7/2016 | Bacon et al. |

FOREIGN PATENT DOCUMENTS

WO 2017/009130 1/2017

OTHER PUBLICATIONS

PCT International Patent Application No. PCT/US18/22151; International Search Report and Written Opinion of the International Searching Authority dated Aug. 3, 2018, 12 pages.
Lumi-Tens. Transcutaneous Electrical Nerve Stimulation Device, GF Health Products, Inc. Operation Manual, Jul. 2008, 15 total pages.
U.S. Appl. No. 15/465,416, filed Mar. 21, 2017.

* cited by examiner

*Primary Examiner* — Lindsey G Wehrheim
(74) *Attorney, Agent, or Firm* — Craig R. Miles; CR Miles P.C.

(57) ABSTRACT

A treatment system including one or more of a wound dressing having one or more of a substrate element, a dressing member disposed on the substrate element, an adhesive element disposed on the substrate element, and a tether connecting the wound dressing to a treatment device.

20 Claims, 13 Drawing Sheets

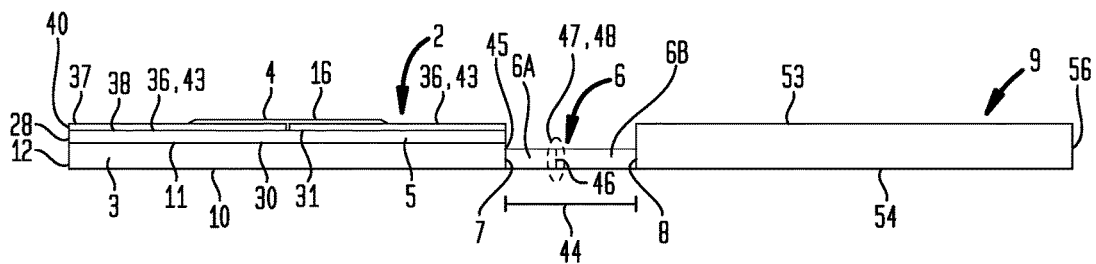
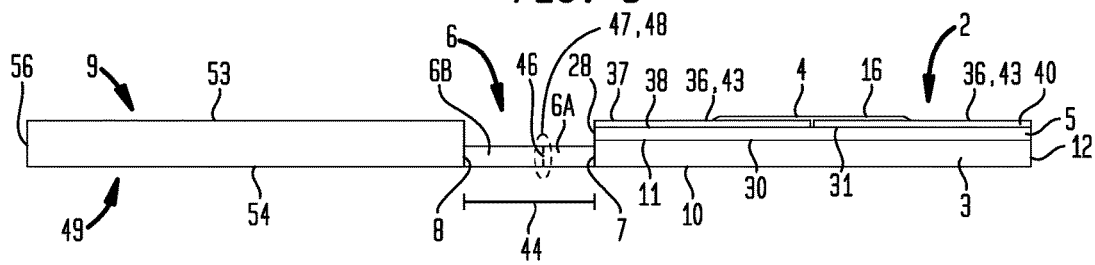
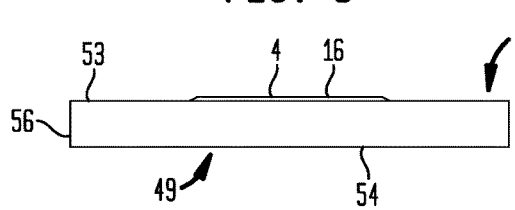
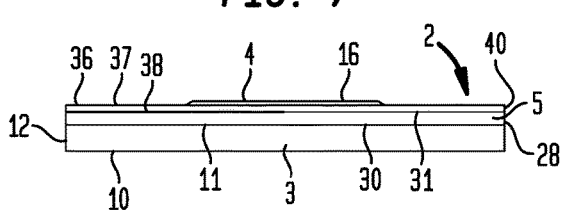

TREATMENT SYSTEM

This U.S. patent application is a continuation-in-part of U.S. patent application Ser. No. 15/465,416, filed Mar. 21, 2017, hereby incorporated by reference herein.

I. FIELD OF THE INVENTION

A treatment system including one or more of a wound dressing having one or more of a substrate element, a dressing member disposed on the substrate element, an adhesive element disposed on the substrate element, and a tether connecting the wound dressing to a treatment device.

II. BACKGROUND OF THE INVENTION

The use of hypodermic needles for medical treatment, such as drug administration and blood sampling, is one aspect of treatment in modern medicine. However, while these procedures promote health, the pain associated with hypodermic needle use often causes patients anxiety in seeking or continuing treatment involving hypodermic needles due to the pain associated with the act of injection. Thus, there would be an advantage in a nerve stimulation system operable to decrease pain associated with hypodermic needle injections.

One form of nerve stimulation to reduce pain is transcutaneous electrical nerve stimulation. Certain embodiments of systems which can perform transcutaneous electrical nerve stimulation include electrodes which deliver electrical stimulus to a targeted portion of a patient's body. In use, transcutaneous electrical nerve stimulation operates by gate control theory. At its most basic, this theory is founded upon a principal of "gates" within the spinal cord which operate to control whether pain signals are transmitted to the brain. The "gates" are open when pain is experienced. Changing the nerve signal to the spinal cord using transcutaneous electrical nerve stimulation alters the signal to the "gate", so that the "gate" closes and no longer allows the pain signal to travel to the brain, so that pain is no longer perceived.

III. SUMMARY OF THE INVENTION

Accordingly, one broad object of the present invention is to provide a treatment system including one or more of a wound dressing and a treatment device, the wound dressing including one or more of a substrate element having a substrate outer edge, a dressing member disposed on the substrate element, an adhesive element disposed on the substrate element between the dressing member and the substrate outer edge, and a tether element having a tether first end connected to the substrate outer edge and a tether second end connected to the treatment device.

Another broad object of the invention is to provide a method of making a treatment system including one or more of providing a substrate element having a substrate outer edge, disposing a dressing member on the substrate element, disposing an adhesive element between the dressing member and the substrate outer edge, disposing a tether length of a tether between a tether first end and a tether second end, connecting the tether first end to the substrate outer edge and connecting the tether second end to a treatment device.

Another broad object of the present invention is to provide a method of using a treatment system including one or more of obtaining a wound dressing including one or more of a substrate element having a substrate outer edge, a dressing member disposed on the substrate element, an adhesive element disposed on the substrate element between the dressing member and the substrate outer edge, and a tether element having a tether first end connected to the substrate outer edge and a tether second end connected to the treatment device, disposing the treatment device on a dressable surface, and disposing the wound dressing over the dressable surface.

Naturally, further objects of the invention are disclosed throughout other areas of the specification, drawings, photographs, and claims.

IV. BRIEF DESCRIPTION OF THE DRAWINGS

FIG. 4 is a side elevation view of a particular embodiment of a treatment system.

FIG. 5 is an opposite side elevation view of a particular embodiment of a treatment system.

FIG. 6 is a back elevation view of a particular embodiment of a treatment system.

FIG. 7 is a front elevation view of a particular embodiment of a treatment system.

V. DETAILED DESCRIPTION OF THE INVENTION

Figure 1:
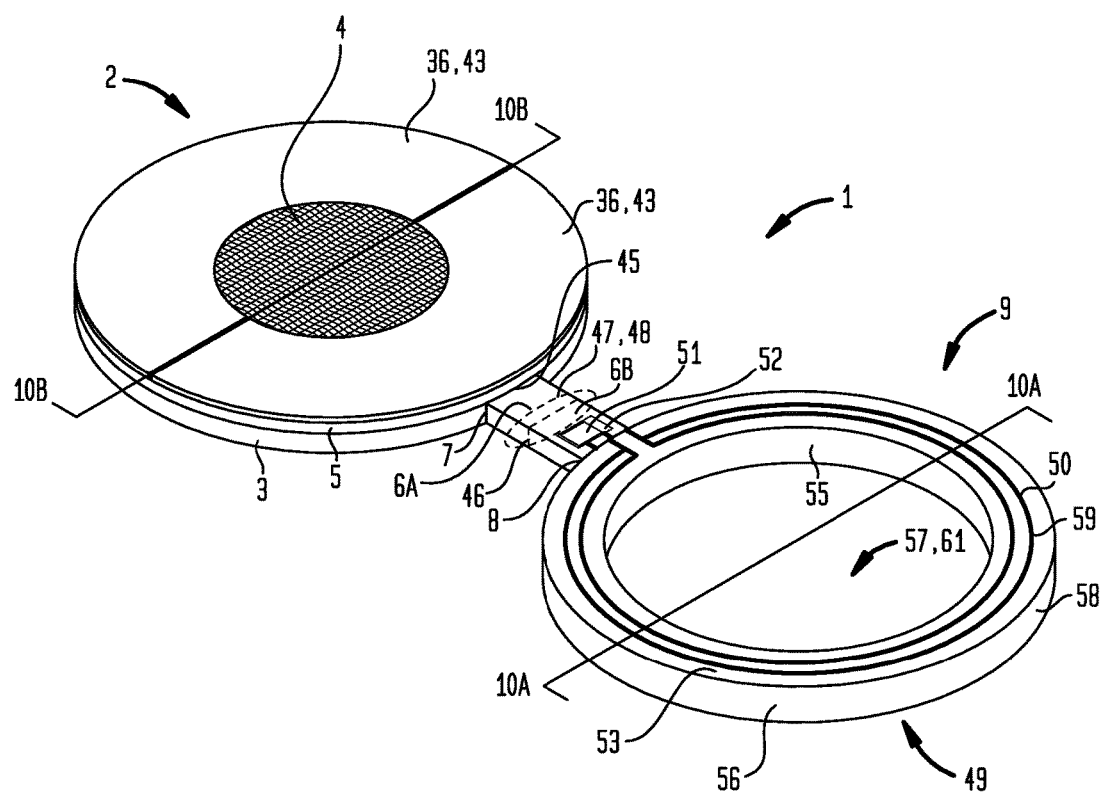
FIG. 1 is a perspective view of a particular embodiment of a treatment system.

A treatment system (1) including one or more of: a wound dressing (2) including a substrate element (3), a dressing member (4), an adhesive element (5), and a tether (6) having a tether first end (7) connected to the substrate element (3) and a tether second end (8) connected to a treatment device (9).

Referring generally to FIGS. 1 through 17, with specific reference to FIGS. 1 through 9 and 10B through 14, particular embodiments of a wound dressing (2) can include a substrate element (3). The substrate element (3) can have a substrate outer face (10) opposite a substrate inner face (11). Both the substrate outer face (10) and the substrate inner face (11) can extend to a substrate outer edge (12). The substrate outer edge (12) can define any regular or irregular geometric figure or other edge configuration for example a square, a rectangle, triangle, a circle, an ellipse, or the like. The substrate element (3) can have an amount of flexure (13). The amount of flexure (13) can permit the substrate element (3) to conform to a dressable surface (14), which can, but need not necessarily, be the epidermis (skin) of an animal, or the surface of an object. The amount of flexure (13) can be sufficient to allow the substrate element (3) to continuously conform during movement of the dressable surface (14), whether by extension, expansion, compression, constriction, or other conformance of the substrate element (3) to the movement of the dressable surface (14). In particular embodiments, the substrate element (3) can, but need not necessarily, further include a plurality of substrate apertures (15) communicating between the substrate outer face (10) and the substrate inner face (11). The substrate element (3) can be a fabric, such as cotton, gauze, or a flexible elastomer or a flexible plastic such as polyvinyl chloride, polyethylene, polyurethane, latex, or paper, or other like material.

Now referring primarily to FIGS. 1, 2, 9, 10B, and 11 through 14, particular embodiments of the treatment system (1) can include a dressing member (4). The dressing member (4) can be disposed on the substrate inner face (11). The dressing member (4) can include a dressing member top surface (16) and a dressing member bottom surface (17) extending to a dressing member peripheral margin (18). The area of the dressing member (4) defined by the dressing member peripheral margin (18) can, but need not necessarily, be less than the area of the substrate element (3). The dressing member peripheral margin (18) can a regular or irregular geometric shape such as a rectangle, square, triangle, circle, ellipse or the like. The dressing member (4) can, but need not necessarily, be disposed centrally on the substrate inner face (11).

Figure 10A:
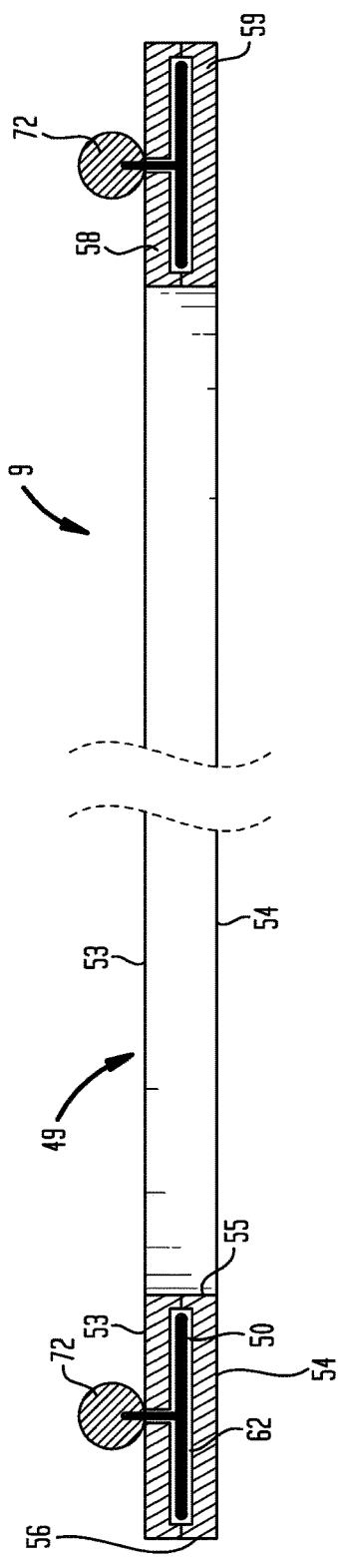
FIG. 10A is a cross-sectional view of 10A-10A of a particular embodiment of a treatment device as shown in FIG. 1.
Figure 10B:
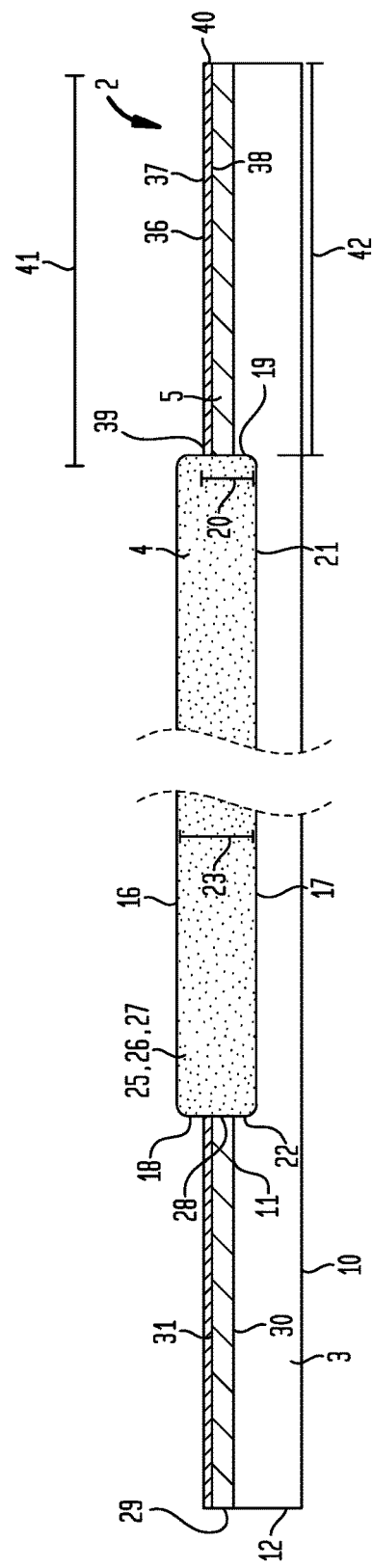
FIG. 10B is a cross-sectional view of 10B-10B of a particular embodiment of a treatment device as shown in FIG. 1.

Now referring primarily to FIG. 10B, in further particular embodiments, the substrate element (3) can, but need not necessarily, include a dressing member recess (19). The dressing member (4) can, but need not necessarily, be disposed in the dressing member recess (19). The dressing member recess (19) can have a recess depth (20) extending from the substrate inner face (11) to a dressing recess bottom surface (21). The dressing member recess (19) can be bound by a dressing recess wall (22). The dressing recess wall (22) can further define a regular or irregular geometric shape such as a rectangle, square, triangle, circle, ellipse or the like. The dressing member peripheral margin (18) can, but need not necessarily, be coupled or directly connected to the dressing recess wall (22). The dressing member bottom surface (17) can, but need not necessarily, be coupled or directly connect to the dressing recess bottom surface (21). The dressing member (4) can have a thickness (23) greater than, less than, or substantially equal to the depth (24) of the dressing member recess (19).

The material of the dressing member (4) can be made of a one or a combination of materials such as: cotton, wool, woven or spun fibers, whether natural or synthetic, or a hydrogel. The material(s) can, but need not necessarily, be materials which absorb liquids. As to particular embodiments, the dressing member (4) can, but need not necessarily, include a thin, porous-polymer coating to keep it from sticking to the wound. The dressing member (4) can, but need not necessarily, include one or more of: a therapeutic or palliative substances (25) and without limitation to the breadth of the foregoing, a topical drug, a dermo-cosmetic cream or lotion, cutaneous steroid, vitamins, an anti-bacterial element (26). The medicament (27), palliative substance (25) or anti-bacterial element (26) can be disposed within the dressing member (4). The anti-bacterial element (26) can be as examples include one or more of mupirocin, bacitracin, polymyxin B, neomycin, clindamycin, gentamicin, or other like anti-bacterial chemical.

Now referring primarily to FIGS. 1 through 9 and FIGS. 10B through 14, particular embodiments of the wound dressing (2) can, but need not necessarily, include an adhesive element (5). The adhesive element (5) can include one or more synthetic or biological adhesives such as: vinyl resins such as an acrylate, including methacrylates and epoxy diacrylates, acrylics, cyanoacrylates, silicone, polyurethane, fibrin, or the like.

In particular embodiments, the adhesive element (5) can include an adhesive element continuously extending over the substrate inner face (11). In particular embodiments, the adhesive element can extend from an adhesive element inner edge (28) to an adhesive element outer edge (29). In particular embodiments, the adhesive element inner edge can be disposed about or congruent with the dressing member peripheral margin (18) or dressing member recess (19) and the adhesive element outer edge (29) can be disposed toward or at the substrate outer edge (12), as exemplified in FIG. 10B. In particular embodiments, the adhesive element (5) can have a thickness between an adhesive element bottom surface (30) affixed to the substrate inner face (11) and an adhesive element top surface (31) adapted to removably secure to a dressable surface (14). The dressable surface (14) can include an epidermis first portion (32) surrounding an epidermis second portion (33) having a dressable wound. For purposes of this invention, "dressable wound" is broadly defined as injury, harm damage, or treatment of or to the epidermis (34), dermis, or underlying tissues including, as illustrative examples one or more of: puncturing, lacerating, abrading, bruising, gashing, burning, blistering, or other injury, harm, damage, or treatment whether intentional in the example of a surgical incision, injection, treatment or topical application of a substance or unintentional, but which can be characterized by injury, harm damage, treatment or application of a substance to the epidermis (34), dermis or underlying tissues. The adhesive element (5) can be removably secured to the epidermis first portion (32) of the dressable surface (14) to dispose the dressing member (4) disposed over epidermis second portion (33) including the dressable wound (35).

Now referring primarily to FIGS. 1 through 9, 10B and 15, further particular embodiments of the treatment system (1) can, but need not necessarily include a peelable layer (36) peelably coupled to the adhesive element. The peelable layer (36) can have a peelable layer top surface (37) and a peelable layer bottom surface (38) extending between a peelable layer inner edge (39) and a peelable layer outer edge (40). The peelable layer (36) can, but need not necessarily, be congruent to the adhesive element (5), where the distance (41) between the peelable layer inner edge (39) and peelable layer outer edge (40) can be substantially equal to the distance (42) between the adhesive element inner edge (28) and the adhesive element outer edge (29). The peelable layer bottom surface (38) can be peelably coupled to the adhesive element top surface (31). The peelable layer (36) can, but need not necessarily, be substantially congruent to the adhesive element top surface (31) and have each of the peelable layer bottom surface (38) and peelable layer top surface (37) extend from the dressing member peripheral margin (18) to the adhesive element outer edge (29). The peelable layer (36) can be a one piece peelable layer (36) or a plurality of peelable layers (43) each peelably coupled to the adhesive element top surface (31).

Now referring primarily to FIGS. 1 through 9 and 11 through 14, further particular embodiments of the treatment system (1) can include a tether (6). The tether (6) can have a length (44) disposed between a tether first end (7) and a tether second end (8). The tether first end (7) can be connected to the substrate outer edge (12). In particular embodiments, the tether first end (7) and the substrate outer edge (12) can be a one piece construct. In other particular embodiments, the tether first end (7) the substrate outer edge (12) can be discrete elements including a fastener (45) which allows removable coupling of the tether first end (7) to the substrate outer edge (12). The fastener (45) can be any of a wide variety of fasteners capable of connecting the tether first end (7) to the substrate outer edge (12), as illustrative examples, a clip, an adhesive, detachably mated portions of a snap, hook and loop material, or the like.

The tether second end (8) can be connected to a treatment device (9). In particular embodiments, the tether second end (8) and the treatment device (9) can be one piece construct. In other particular embodiments, the tether second end (8) and the and the treatment device (9) can be discrete elements including a fastener which allows removable coupling of the tether second end (8) to the treatment device. The fastener (45) can be any of a wide variety of fasteners capable of connecting the tether first end (7) to the substrate outer edge (12), as illustrative examples, a clip, an adhesive, detachably mated portions of a snap, hook and loop material, or the like.

Figure 16:
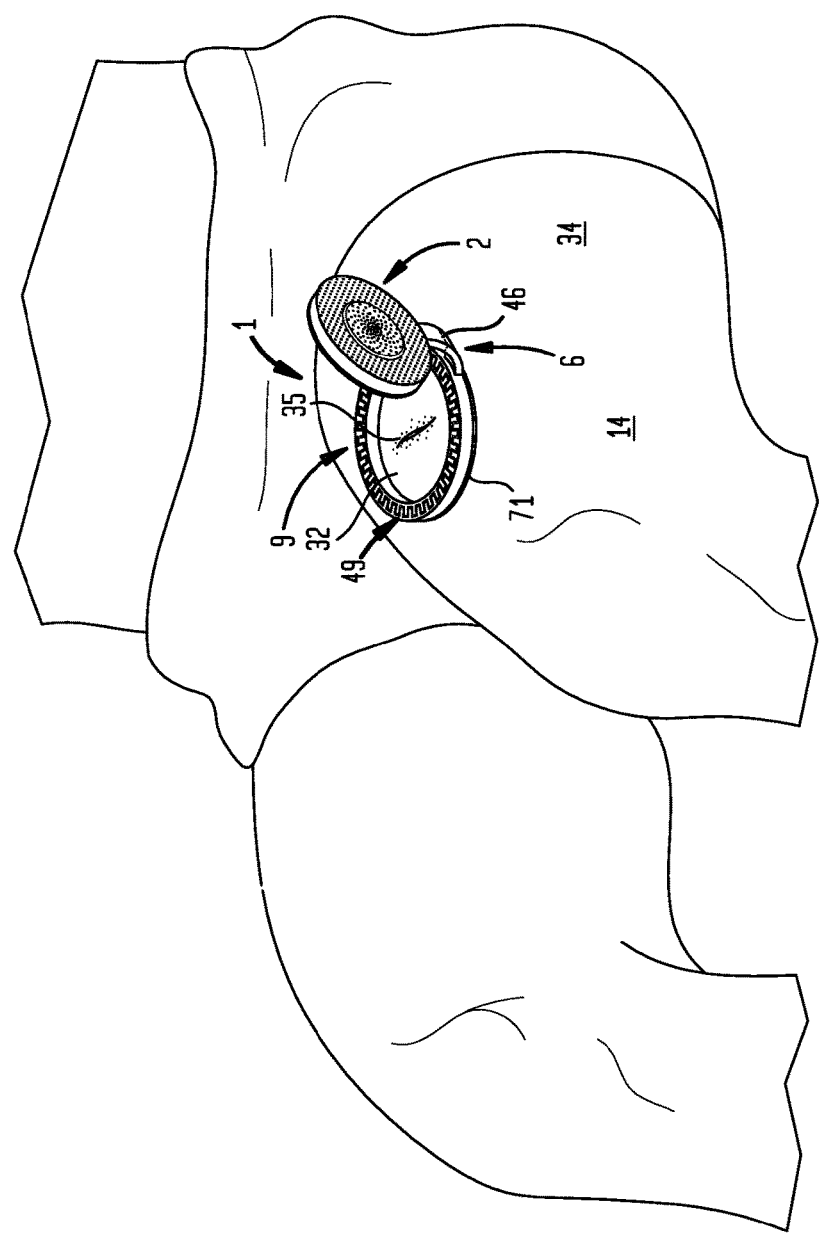
FIG. 16 is a perspective view illustrating a method of using a particular embodiment of a treatment system.

In particular embodiments, the tether (6) can, but need not necessarily, include an amount of flexure (13) between the tether first end (7) and the tether second end (8) to permit the wound dressing (2) to be positionally adjusted in relation to the treatment device (9). For example, as shown in FIG. 16, the tether (6) can be flex or fold to allow movement of the wound dressing (2) in relation to the treatment device (9). The tether (6) can be of the same material as the substrate element (3) or a different material from that of the substrate element (3). The tether (6) can include one or more of a fabric, such as cotton, gauze, or a flexible elastomer or a flexible plastic such as polyvinyl chloride, polyethylene, polyurethane, latex, or paper, or other like material.

Figure 17:
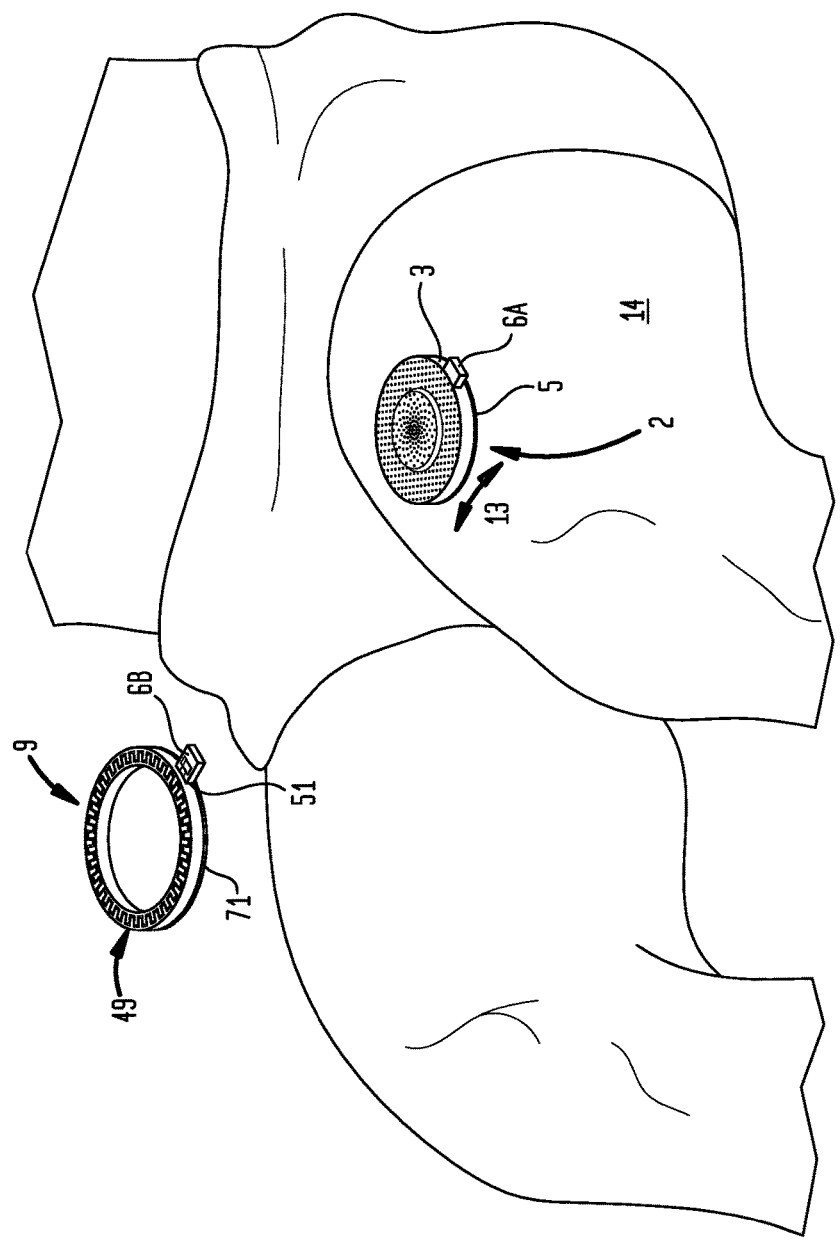
FIG. 17 is a perspective view illustrating a method of using a particular embodiment of a treatment system.

Now referring primarily to FIGS. 16 and 17, in particular embodiments, the tether (6) can be severable to detach the wound dressing (2) from the treatment device (9). Severance of the tether (6) can be achieved by repeated manipulation of the tether (6) to cause mechanical failure of the tether (6), cutting the tether (6) with a scalpel, knife or scissors, forcibly pulling on the tether first end (7) and the tether second end (8) in opposing directions, or other like manner of severing the tether (6) into at least two portions (6A)(6B).

Now referring primarily to FIGS. 1 through 9 and 11 through 14, in further particular embodiments, the tether (6) can, but need not necessarily, include a severance element (46). The severance element (46) operates to sever the tether (6) in a pre-selected severance area (47) allowing the wound dressing (2) to detach from the treatment device (9). The severance element (46) can be a structurally weakened area (48) of the tether (6) more susceptible to being severed than the remainder of the tether (6). As an illustrative example, the severance element (46) can be a line of perforations in the tether which provide a tear path in the pre-selected severance area (47), as illustrated in FIG. 1. However, other configurations of the severance element (46) are contemplated such as a reduction in the thickness or width of the tether (6) or partial cutting the tether (6) in the pre-selected severance area (47), or other like method of structural weakening. The severance element (46) can be disposed in the tether (6) at the tether first end (7) or the tether second end (8), or between the tether first end (7) and the tether second end (8).

Generally referring to FIGS. 1 through 10A and 11 through 14, a treatment device (9) can include one or more of an annular frame (49), an electrically conductive element (50), a controller (51) and a power source (52). The annular frame (49) can have a top surface (53) and bottom surface (54) extending between an inner annular wall (55) and an outer annular wall (56). The inner annular wall (55) can define an annular frame aperture (57) communicating between the top surface (53) and the bottom surface (54) of the annular frame (49). In particular embodiments, the annular frame (49) can have a non-electrically conductive top surface (53) comprised of a non-electrically conductive material (58), as illustrative examples: plastic, a fabric such as cotton, wool, or linen, or combinations thereof, and an electrically conductive bottom surface (54) comprised of an electrically conductive material (59) capable of conducting current (60), as illustrative examples: carbonized silicone rubber, carbon impregnated plastic, conductive carbon film or gel, hydrogel layers, or combination thereof. The non-electrically conductive top surface (53) and the electrically conductive bottom surface (54) can extend from the inner annular wall (55) to the outer annular wall (56). While the Figures show, the inner annular wall (55) and the outer annular wall (56) generally orthogonal to the non-electrically conductive top surface (53) and electrically conductive bottom surface (54); this is not intended to preclude, embodiments in which one or both of the inner annular wall (55) or the outer annular wall (56) can be disposed at an angle or in arcuate relation to the non-electrically conductive top surface (6) and electrically conductive bottom surface (54).

Figure 2:
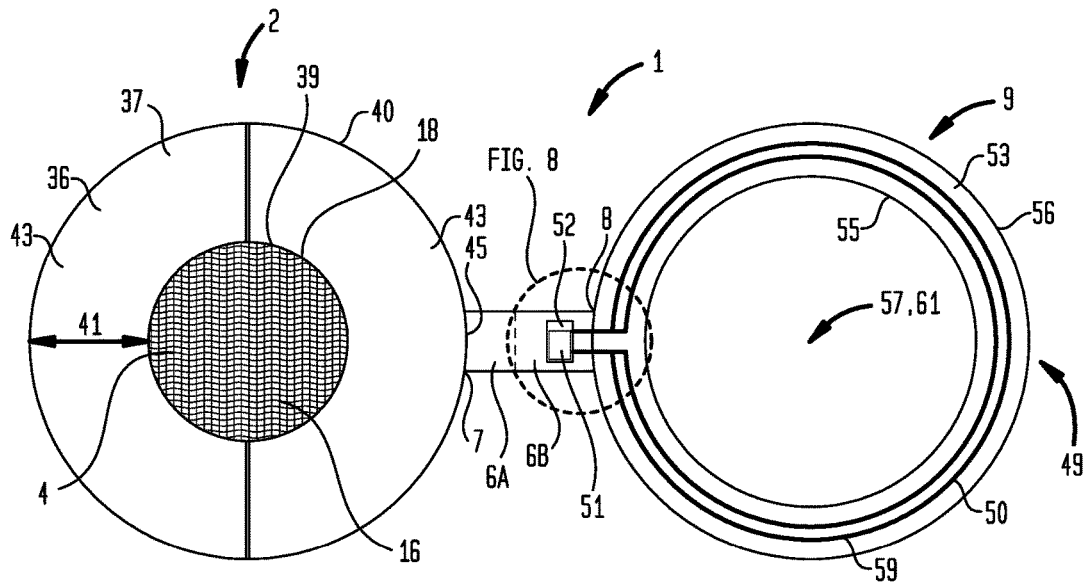
FIG. 2 is a top plan view of a particular embodiment of a treatment system.
Figure 3:
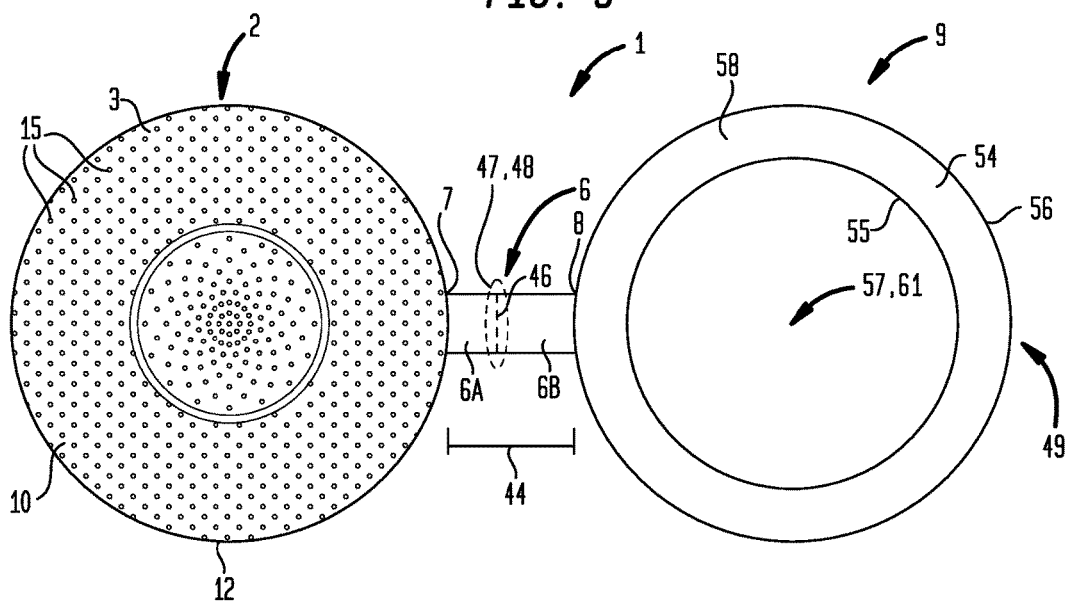
FIG. 3 is a bottom plan view of a particular embodiment of a treatment system.

In particular embodiments, the annular frame (49) can have generally circular inner and outer annular walls (55) (56) with the inner annular wall (55) defining a circular frame aperture (61) (as shown in the example of FIG. 2). However, this is not intended to preclude embodiments in which the annular frame (49) defines a square, rectangle, diamond, triangle, or other geometric shape having a continuous perimeter, and having an inner annular wall (55) correspondingly defining an annular frame aperture (57) configured as a square, rectangle, or other geometric shape.

Now referring primarily to FIGS. 10A and 11 through 14, in particular embodiments, the annular frame (49) can have an annular frame channel (62) disposed between the inner annular wall (55) and the outer annular wall (56) and between the non-electrically conductive top surface (53) and the electrically conductive bottom surface (54), and electrically connected to the electrically conductive bottom surface (54). An electrically conductive element (50) can be disposed in the annular frame channel (62).

Now referring primarily to FIGS. 11 through 14, in particular embodiments, the electrically conductive element (50) can comprise a plurality of discrete electrically conductive elements (63) each correspondingly disposed in a plurality of discrete annular frame channels (64).

Figure 11:
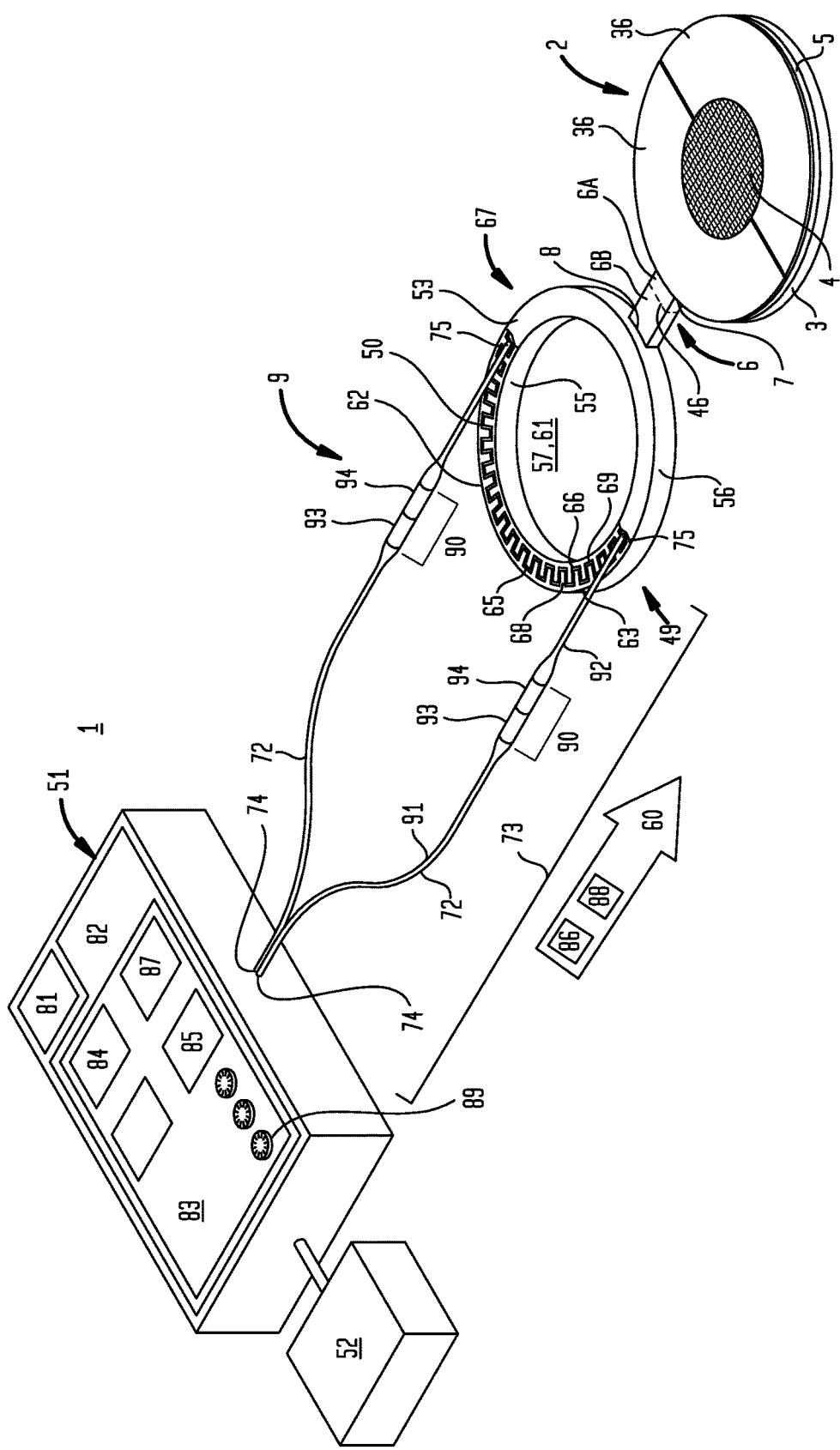
FIG. 11 is a perspective view of a particular embodiment of a treatment system including a power source and controller.
Figure 12:
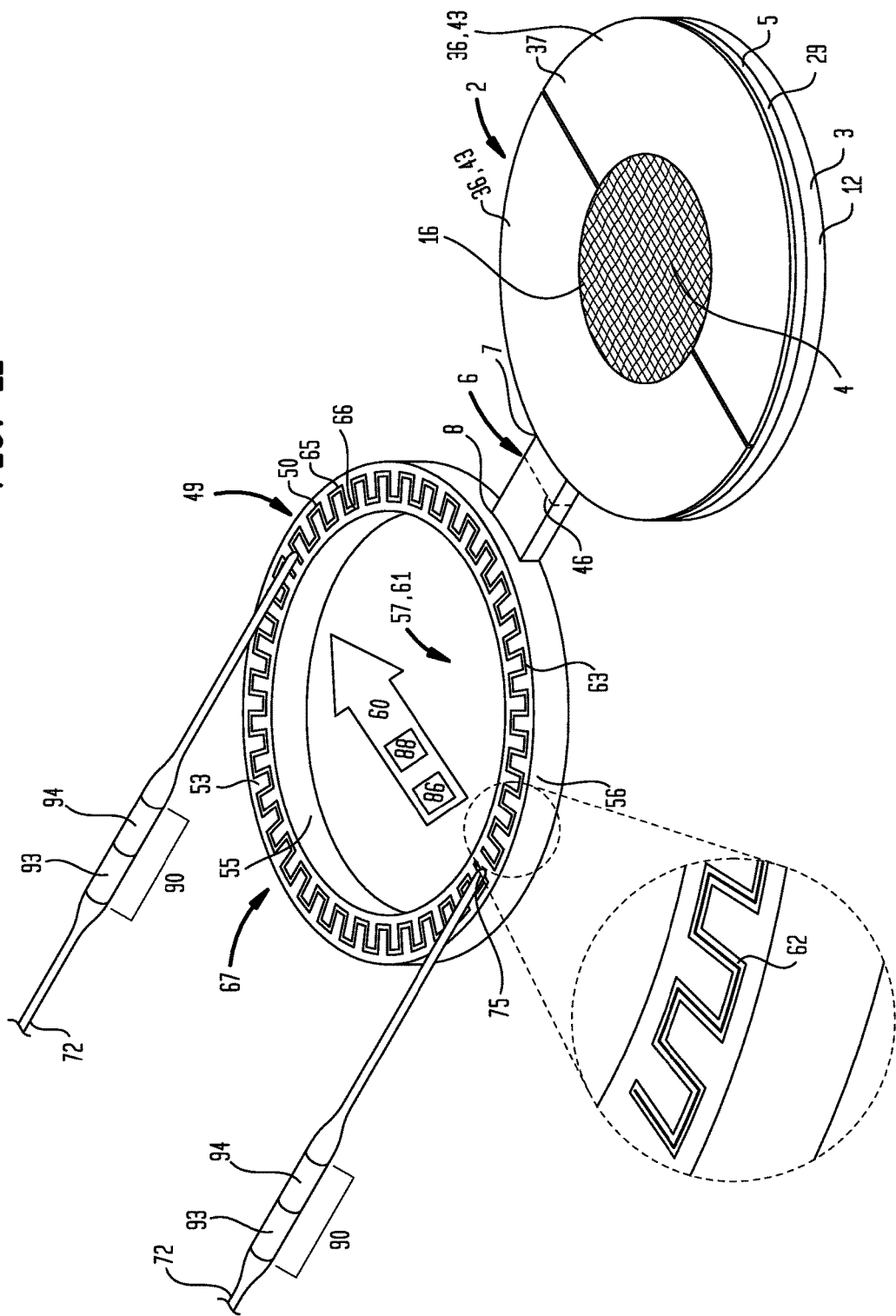
FIG. 12 is an enlarged perspective view of a particular embodiment of a treatment system.

Referring now to FIGS. 11 and 12, a first annular frame channel (65) can be disposed in opposite relation to a second annular frame channel (66) between a non-electrically conductive top surface (53) and an electrically conductive bottom surface (54) in a first configuration (67). A first electrically conductive element (50) and a second electrically conductive element (50) can be correspondingly disposed in the first and second annular frame channels (65)(66). The power source (52) can be discretely connected to each of the first and second electrically conductive elements (68)(69).

Figure 13:
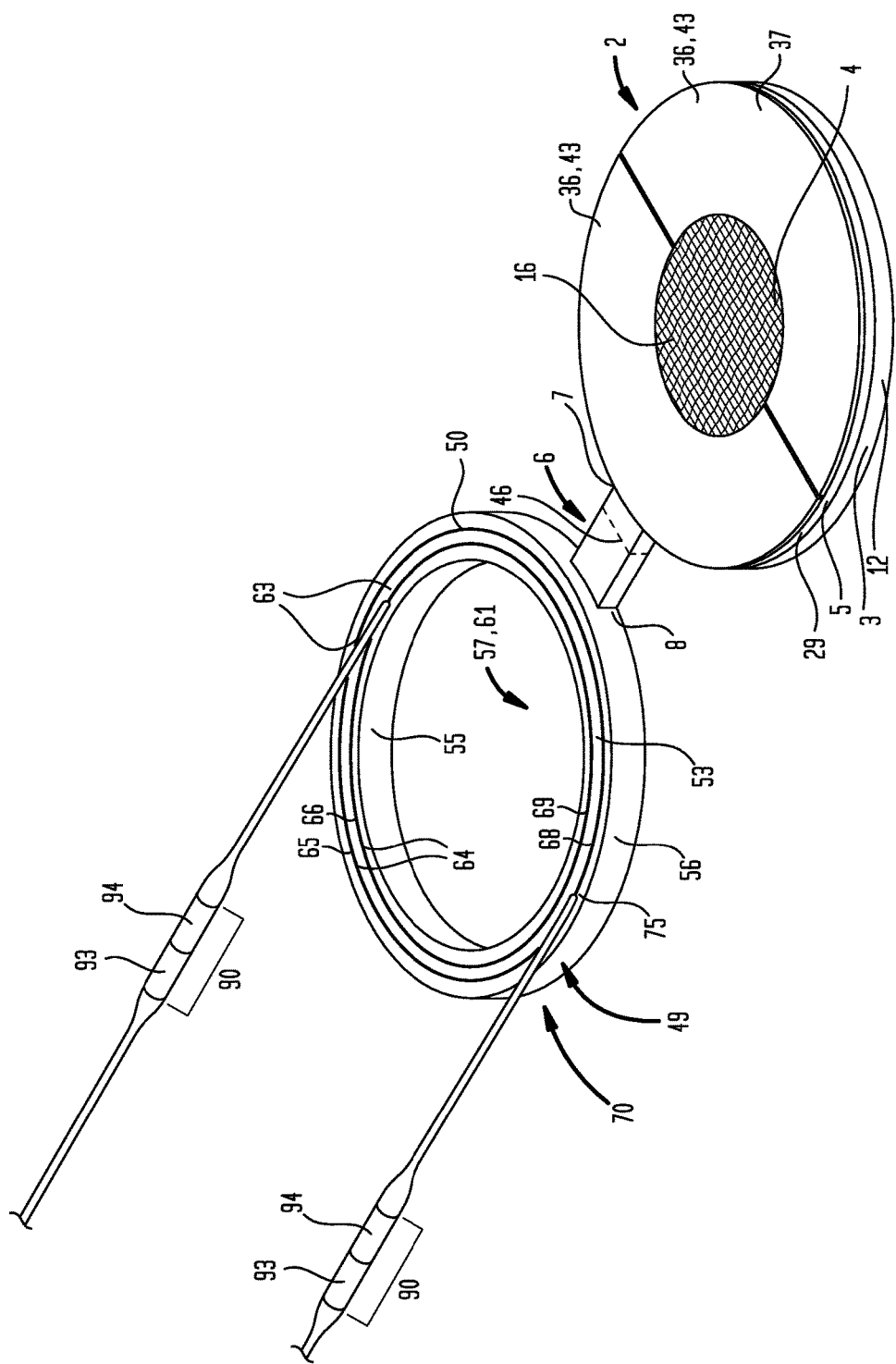
FIG. 13 is an enlarged perspective view of another particular embodiment of a treatment system.
Figure 14:
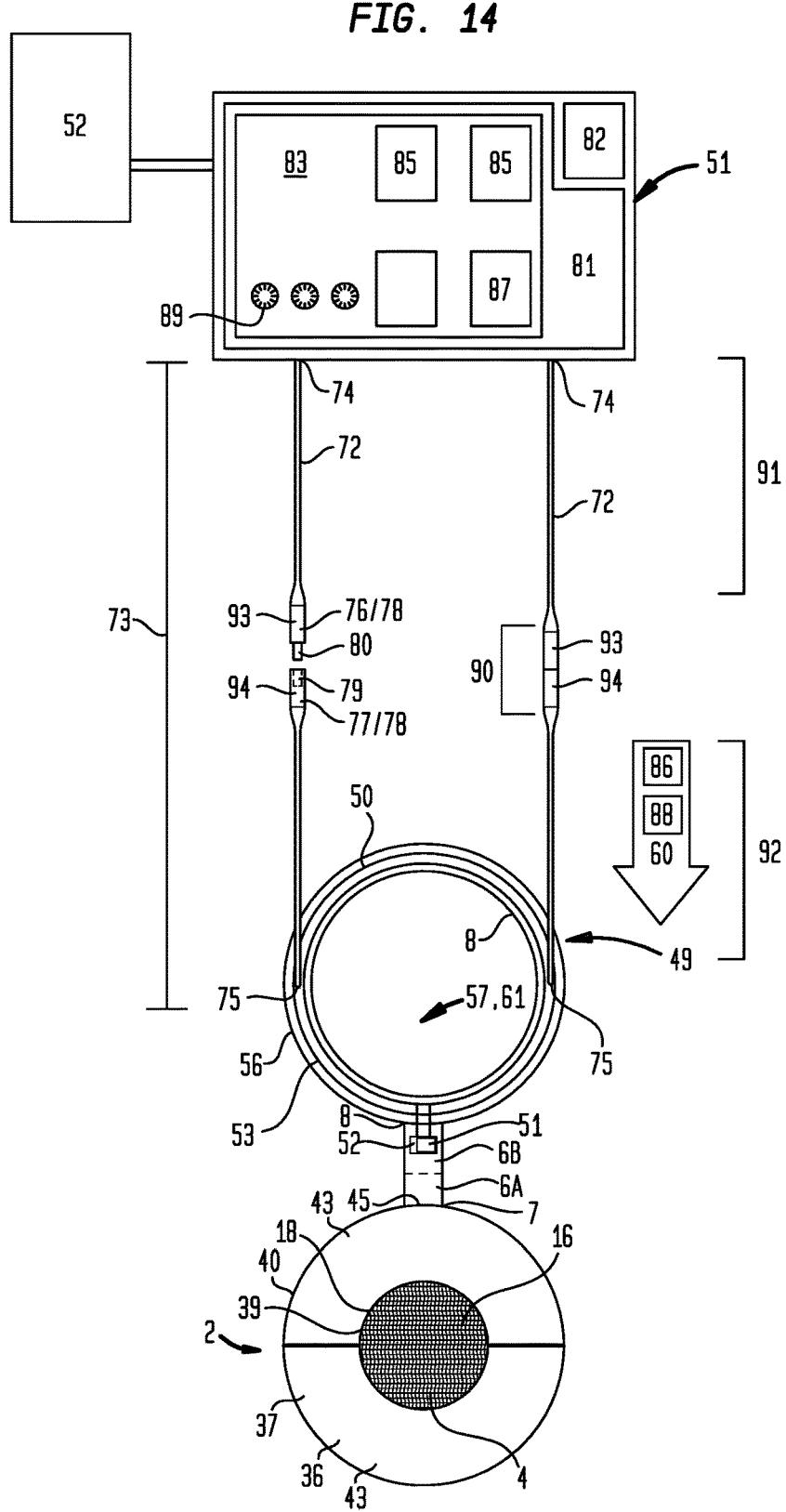
FIG. 14 is a top plan view of a particular embodiment of a treatment system having a controller and power source.

Referring now to FIGS. 13 and 14, a plurality of discrete electrically conductive elements (63) can be disposed in a plurality of discrete annular frame channels (64) in a second configuration (70). A first annular frame channel (65) and a second annular frame channel (66) can be circumferentially disposed in parallel relation a distance apart between a non-electrically conductive top surface (53) and an electrically conductive bottom surface (54). A first electrically conductive element (50) and a second electrically conductive element (50) can be correspondingly disposed in a first annular frame channel (65) and a second annular frame channel (66). The power source (52) can be discretely connected to each of the first and second electrically conductive elements (68)(69).

The electrically conductive element (50) can comprise a wide variety of materials capable of conducting a current (60) including or consisting of: copper, silver, gold, beryllium copper, phosphor bronze, zirconium copper, constantan, MANGANIN, nickel, steel, or combinations thereof.

Figure 15:
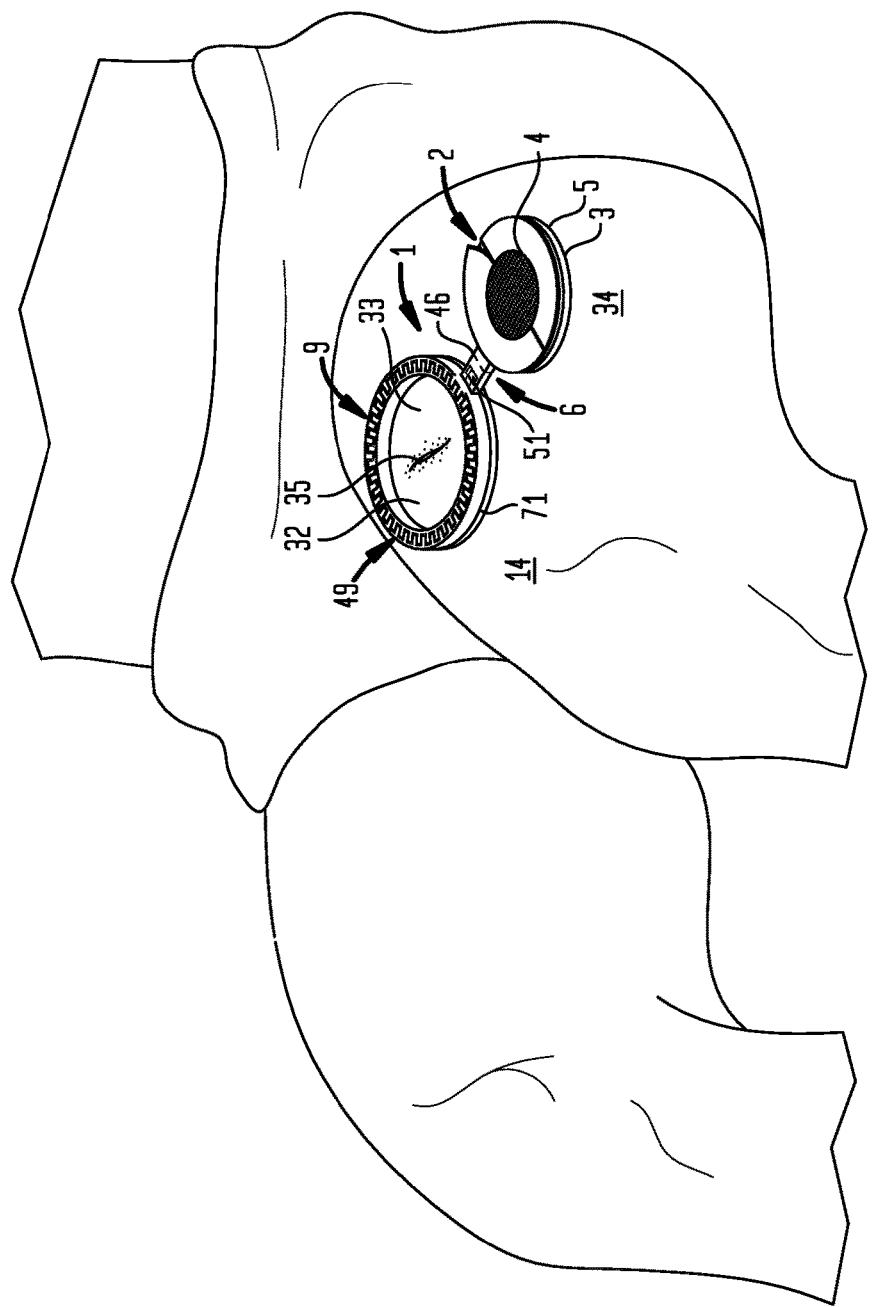
FIG. 15 is a perspective view illustrating a method of using a particular embodiment of a treatment system.

Now referring primarily to FIG. 15, particular embodiments of the treatment device (9) can, but need not necessarily, include an adhesion layer (71) coupled to the electrically conductive bottom surface (54) of the annular frame (49). The adhesion layer (71) can comprise a pressure sensitive or wet adhesion layer. A pressure sensitive adhesive can be described as a viscous and tacky material capable of wetting a surface on contact, which bonds with the contact surface with the application of pressure. The material comprising the pressure sensitive adhesive can be rubber-based, acrylic-based, silicone-based, or other like material, or combinations thereof. A wet adhesion layer can be described as a viscous gel or other conductive liquid medium that operates to facilitate the transfer of current (60) from the conducting material to the object receiving the current (60). In further particular embodiments, the adhesion layer (71) can be capable of increasing, decreasing, or maintaining the strength of the current (60) generated by the electrically conductive element (50). The capability of the adhesion layer (71) to manipulate the strength of the current (60) can be obtained by the addition of an impurity to the materials comprising the adhesion layer (71), where the impurity alters the conduction characteristics of the adhesion layer (71)

Now referring primarily to FIGS. 1 through 8, 11, and 14, a treatment device (9) can include a power source (52). The power source (52) can be electrically coupled to the electrically conductive element (50) and capable of generating a current (60) to and through the electrically conductive element (50). In particular embodiments, the power source (52) can comprise a direct current source such as a battery or an alternating current source such as a 120 volt outlet with an alternating current adapter coupled to an electrical outlet to convert the alternating current to direct current, or other like electrical power source (52), or combinations thereof.

In particular embodiments of a treatment device (9), the power source (52) can be electrically coupled to the electrically conductive element (50) by utilizing a plurality of leadwires (72). Each of the one or more leadwires (72) can have a length (73) disposed between a leadwire first end (74) and a leadwire second end (75). In particular embodiments, coupling of each of the plurality of leadwires (72) can be achieved by configuring the leadwire first end (74) as a male or female connector (76)(77) which can be insertingly engaged to a complementary male or female connector (76)(77) disposed on the controller (51) and the leadwire second end (75) can be integrated to the electrically conductive element (50). In other particular embodiments, the leadwire first end (74) can be integrated with the controller (51) and the leadwire second end (75) can be configured as a male or female connector (76)(77) which can be insertingly engaged to a complementary male or female connector (76)(77) disposed on the electrically conductive element (50).

In other particular embodiments, the leadwire first end (74) can be integrated to the controller (51) and the leadwire second end (75) can be integrated to the electrically conductive element (50). In other particular embodiments the leadwire first end (74) can be configured as a male or female connector (76)(77) and insertingly engaged to a complementary male or female connector (76)(77) disposed on the controller (51) and the leadwire second end (75) can be configured as a male or female connector (76)(77) which can be insertingly engaged to a complementary male or female connector (76)(77) disposed on the electrically conductive element (50). Each of the plurality of leadwires (72) can be coupled to the controller (51) and the electrically conductive element (50) by utilizing the same configuration or combination of configurations described above.

For purposes of this invention, the term female connector (77) means a connector (78) attached to a leadwire (72) having one or more recessed holes (79) with electrical terminals (80) inside configured to accept a male connector (76), and the term male connector (76) means a connector (78) having exposed electrical terminal(s) (80) and configured to be received in a female connector (77). The leadwire (72) can be comprised of a leadwire conducting material encased within a non-conducting material. The leadwire conducting material can include or consist of: copper, a copper alloy, tinsel wire, silver, gold, or other like conducting material, or combinations thereof. The non-conducting material can include or consist of: silicone, polyvinyl chloride, thermoplastic elastomer, thermoplastic rubber, thermoplastic polyurethane, or other like non-conducting material.

Figure 8:
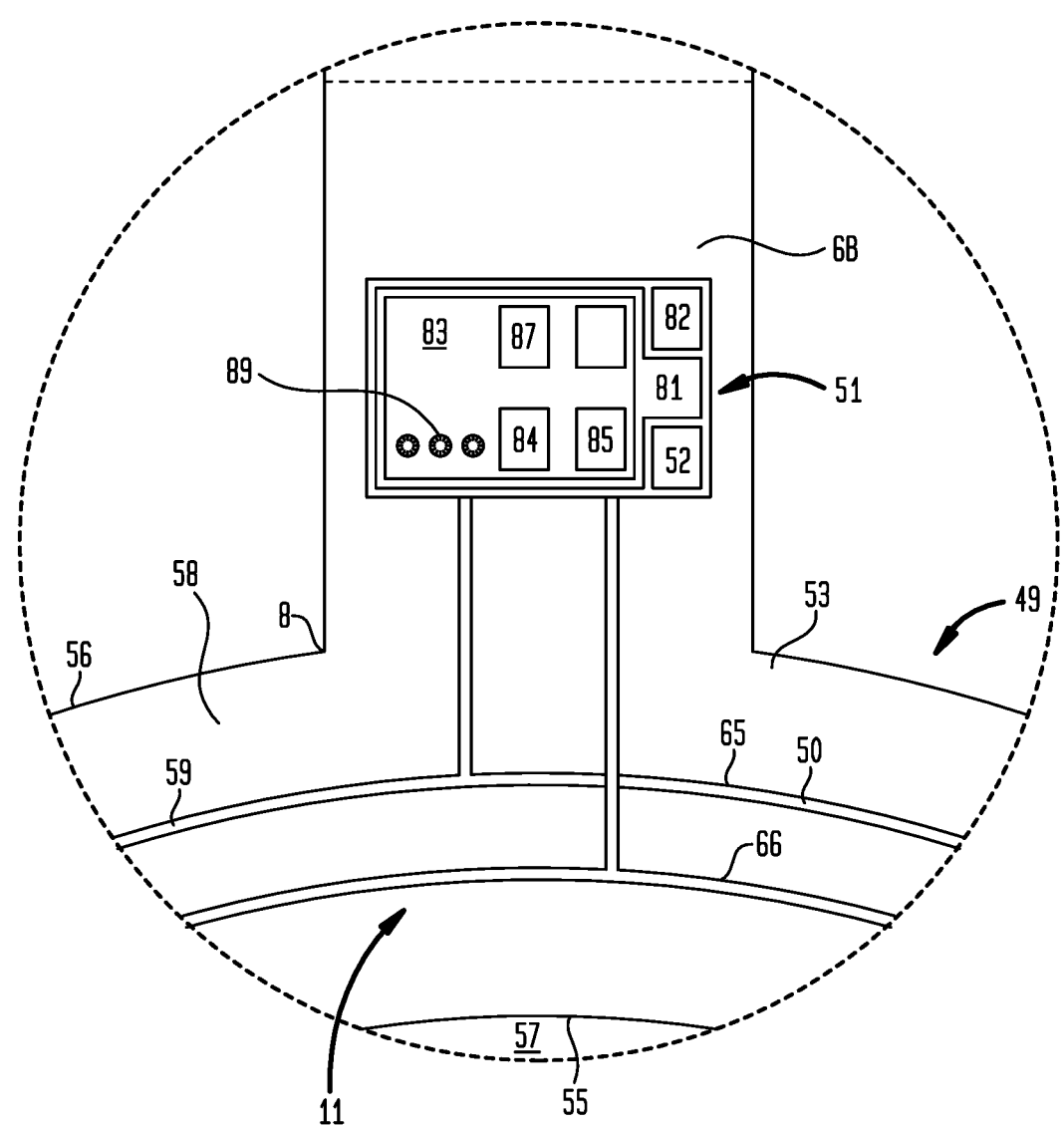
FIG. 8 is an enlarged view of a particular embodiment of a treatment system including a power source and a controller.
Figure 9:
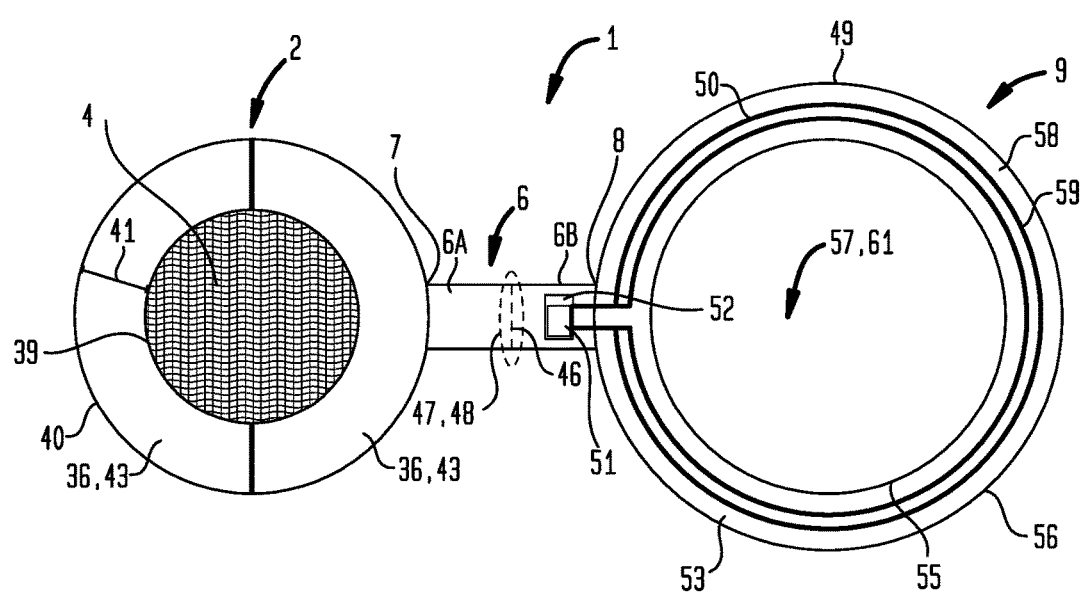
FIG. 9 is a top elevation view of another particular embodiment of a treatment system.

Now referring primarily to FIGS. 8, 11, and 14, the treatment device (9) can include a controller (51). The controller (51) can be electrically coupled to the power source (52) and the electrically conductive element (50). In particular embodiments, the power source (52) can be integrated into the controller (51) as a single unit electrically coupled to the electrically conductive element (50), or the power source (52) can be externally electrically coupled to the controller (51), which can be electrically coupled to the electrically conductive element (50) (as shown in FIG. 1). The controller (51) can further include a processor (81) communicatively coupled to a memory element (82) containing a program (83) executable to periodically electrically couple or uncouple the power source (52) to or from the electrically conductive element (50).

In particular embodiments, the program (83) can include a current regulation module (84) executable to electrically couple the power source (52) to the electrically conductive element (50) to deliver a current (60) between about 0 mA to about 100 mA. In particular embodiments, the current (60) can be selected from the group including or consisting of: about 1 milliamp ("mA") to about 10 mA, about 5 mA to about 15 mA, about 10 mA to about 20 mA, about 15 mA to about 25 mA, about 20 mA to about 30 mA, about 25 mA to about 35 mA, about 30 mA to about 40 mA, about 35 mA to about 45 mA, about 40 mA to about 50 mA, about 45 mA to about 55 mA, about 50 mA to about 60 mA, about 55 mA to about 65 mA, about 60 mA to about 70 mA, about 65 mA to about 75 mA, about 70 mA to about 80 mA, about 75 mA to about 85 mA, about 80 mA to about 90 mA, about 85 mA to about 95 mA, and about 90 mA to about 99 mA, or combinations thereof.

In further particular embodiments, the program (83) can further include a pulse rate generator (85) executable to electrically couple and uncouple the power source (52) to and from the electrically conductive element (50) at a current pulse rate (86). For purposes of this invention, the term current pulse rate (86) means the number of times the power source (52) electrically couples and uncouples to and from the electrically conductive element (50) over a duration of time. The current pulse rate (86) can be between about 1 pulse per second ("pps") to about 250 pulses per second. In further particular embodiments, the current pulse rate (86) can be selected from the group consisting of about 5 pps to about 20 pps, about 10 pps to about 30 pps, about 20 pps to about 40 pps, about 30 pps to about 50 pps, about 40 pps to about 60 pps, about 50 pps to about 70 pps, about 60 pps to about 80 pps, about 70 pps to about 90 pps, about 80 pps to about 100 pps, about 90 pps to about 110 pps, about 100 pps to about 120 pps, about 110 pps to about 130 pps, about 120 pps to about 140 pps, about 130 pps to about 150 pps, about 140 pps to about 160 pps, about 150 pps to about 170 pps, about 160 pps to about 180 pps, about 170 pps to about 190 pps, about 180 pps to about 200 pps, about 210 pps to about 230 pps, about 220 pps to about 240 pps, and about 230 pps to about 245 pps, or combinations thereof.

In further particular embodiments, the program (83) can further include a pulse width generator (87) that can be executable to electrically couple and uncouple the power source (52) to and from the electrically conductive element (50) at a current pulse width (88) between about 1 millisecond ("ms") to about 250 ms. In further particular embodiments, the current pulse width (88) can be selected from the group consisting of about 5 ms to about 20 ms, about 10 ms to about 30 ms, about 20 ms to about 40 ms, about 30 ms to about 50 ms, about 40 ms to about 60 ms, about 50 ms to about 70 ms, about 60 ms to about 80 ms, about 70 ms to about 90 ms, about 80 ms to about 100 ms, about 90 ms to about 110 ms, about 100 ms to about 120 ms, about 110 ms to about 130 ms, about 120 ms to about 140 ms, about 130 ms to about 150 ms, about 140 ms to about 160 ms, about 150 ms to about 170 ms, about 160 ms to about 180 ms, about 170 ms to about 190 ms, about 180 ms to about 200 ms, about 210 ms to about 230 ms, about 220 ms to about 240 ms, and about 230 ms to about 245 ms, or combinations thereof.

In particular embodiments, the controller (51) can further include an interface (89) operable by a user of the treatment device (9). The interface (89) can enable a user to select a current (60), current pulse rate, and a pulse width. The interface (89) can be a graphical interface, such as a push-button interface, touch screen, or other like graphical interface. The interface (89) can also be a series of marked dials maneuverable by the user to make a selection.

Now referring primarily to FIG. 14, particular embodiments of the treatment device (9) can include one or more breaker elements (90). A breaker element (90) can be disposed at a location along the length (73) of the leadwire (72) between the leadwire first end (74) and the leadwire second end (75) to define a leadwire first portion (91) coupled to the controller (51) and a leadwire second portion (92) coupled to the electrically conductive element (50). The breaker element (90) can be configured to have a first connector (93) and a second connector (94) capable of electrically coupling and uncoupling the electrically conductive element (50) and the power source (52) along the length (73) of the leadwire (72) by matingly engaging or disengaging the first connector (93) and second connector (94) of the breaker element (90). As an illustrative example, FIG. 6 shows the flow of current (60) through a treatment device (9) when the first connector (93) and second connector (94) of the breaker element (90) is matingly engaged. FIG. 12 shows the flow of current (60) through a treatment device (9) when the first connector (93) and second connector (94) of the breaker element (90) is not matingly engaged. The breaker element (90) can be utilized to rapidly disrupt the operation of the treatment device (9) by matingly disengaging the first connector (93) and second connector (94) to interrupt the electrical coupling of the power source (52) and the electrically conductive element (50).

Now referring generally to FIGS. 15 through 17, particular methods of using a treatment system (1) can include one or more of obtaining a wound dressing (2) tethered to a treatment device (9), which includes one or more of a substrate element (3), a dressing member (4), a tether (6), and a treatment device (9), as described above, disposing the treatment device (9) about a dressable wound (35) on a dressable surface (14), and folding the tether (6) to dispose the wound dressing (2) over the dressable surface (14). The method can further include adhering the adhesive element (5) to the dressable surface (14). In embodiments including a peelable layer (36), the method can further include peeling a peelable layer (36) from the adhesive element (5). The method can further include severing the tether (6) and further include detaching the treatment device (9) from the wound dressing (2). The method can further include severing of the tether (6) at a severance element (46) in a pre-selected severance area (47) of the tether (6).

In particular embodiments including a treatment device (9) having an annular frame (49), the method of using a treatment system (1) can further include disposing the annular frame on an epidermis (34) of an animal to dispose a dressable wound (35) within the annular frame aperture (57), and folding the tether (6) to dispose the wound dressing (2) inside the annular frame aperture (57) of the treatment device (9) over the dressable wound (35).

Further methods of using particular embodiments of the treatment system (1) can include one or more of obtaining a treatment device (9), which includes one or more of an annular frame (49), an electrically conductive element (50), a power source (52), and a controller (51). The method can further include, disposing an annular frame (49) on an epidermis (34), selecting a program (83) contained in a non-transitory memory element (82) communicatively coupled to a processor (81) of the controller (51), and executing the program (83) to cause a current (60) from the power source (52) to be delivered to an electrically conductive element (50) in the annular frame; the annular frame (49), electrically conductive element (50), power source (52), and controller (51) being described above. In further particular embodiments of using the treatment device (9), the program (83) can be executed to periodically couple or uncouple the power source (52) from the electrically conductive element (50) to generate a current (60) having a current pulse rate (86), a current pulse width (88), or combination thereof, as described above. In particular embodiments having an adhesion layer (71) coupled to the bottom surface (54) of the annular frame (49), the method of using the treatment device (9) can further include coupling and uncoupling the adhesion layer (71) to the epidermis (34) to spatially position the annular frame (49) on the epidermis (34).

As can be easily understood from the foregoing, the basic concepts of the present invention may be embodied in a variety of ways. The invention involves numerous and varied embodiments of a treatment device and methods for making and using such a treatment device, including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "tether" should be understood to encompass disclosure of the act of "tethering"—whether explicitly discussed or not—and, conversely, were there effectively disclosure of the act of "tethering", such a disclosure should be understood to encompass disclosure of a "tether" and even a "means for tethering." Such alternative teens for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the treatment devices herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

I claim:

1. A treatment system, comprising:
a wound dressing including:
a substrate element having a substrate outer face opposite a substrate inner face, said substrate outer face and inner face extending to a substrate outer edge;
a dressing member disposed on said substrate inner face;
an adhesive element disposed on said substrate inner face between said dressing member and said substrate outer edge; and
a tether having a tether length disposed between tether first and second ends, said tether first end connected to said substrate outer edge and said tether second end connected to a treatment device.

2. The system of claim 1, further comprises an antibacterial element disposed in said dressing member.

3. The system of claim 1, wherein said adhesive element adapted to removably secure to a dressable surface to dispose said dressing member over a dressable wound.

4. The system of claim 3, further comprising a peelable layer removably coupled to said adhesion element.

5. The system of claim 1, wherein said tether capable of being severed to detach said wound dressing from said treatment device.

6. The system of claim 5, further comprising a severance element disposed in said tether, said severance element severs in a pre-selected severance area to detach said wound dressing from said treatment device.

7. The system of claim 1, wherein said tether element capable of being folded to allow movement of said wound dressing in relation to said treatment device.

8. The system of claim 7, wherein said treatment device includes an annular frame having a top surface and a bottom surface extending between an inner annular wall and an outer annular wall, said inner annular wall defining a frame aperture communicating between said top surface and said bottom surface of said annular frame, said tether element foldables to dispose said wound dressing inside of said frame aperture of said treatment device.

9. The system of claim 8, wherein said tether configured to be severed to detach said wound dressing from said treatment device.

10. The system of claim 9, further comprising a severance element disposed in said tether, said severance element severs in a pre-selected severance area to detach said wound dressing from said treatment device.

11. The system of claim 8, wherein said top surface comprises an electrically non-conductive top surface and wherein said bottom surface comprises an electrically conductive bottom surface, and further comprising:
an annular frame channel circumferentially disposed in said annular frame between said electrically non-conductive top surface and said electrically conductive bottom surface;
an electrically conductive element disposed in said annular frame channel, said electrically conductive element electrically connected to said electrically conductive bottom surface; and
a power source electrically coupled to said electrically conductive element.

12. The system of claim 11, wherein said annular frame channel comprises a first annular frame channel and a second annular frame channel circumferentially disposed in parallel relation a distance apart between said non-electrically conductive top surface and said electrically conductive bottom surface;
wherein said electrically conductive member comprises a first electrically conductive element and a second electrically conductive element, each of said first and second electrically conductive elements disposed within a corresponding one of said first and second annular frame channels; and
wherein said power source discretely electrically coupled to each of said first and second electrically conductive elements.

13. The system of claim 11, wherein said annular frame channel comprises a first annular frame channel and a second annular frame channel disposed in opposite relation between said non-electrically conductive top surface and said electrically conductive bottom surface;
wherein said electrically conductive member comprises a first electrically conductive element and a second electrically conductive element each correspondingly disposed in one of said first and second annular frame channels; and
a power source discretely coupled to each of said first and second electrically conductive elements.

14. The system of claim 11, wherein said power source comprises a direct current source or an alternating current source, wherein an alternating current delivered from said alternating current source is converted to a direct current.

15. The system of claim 14, wherein said power source switchably connected to said electrically conductive element delivers a current of about 0 mA to about 100 mA.

16. The system of claim 15, wherein said current is selected from the group consisting of: about 1 mA to about 10 mA, about 5 mA to about 15 mA, about 10 mA to about 20 mA, about 15 mA to about 25 mA, about 20mA to about 30mA, about 25 mA to about 35 mA, about 30 mA to about 40 mA, about 35 mA to about 45 mA, about 40 mA to about 50 mA, about 45 mA to about 55 mA, about 50 mA to about 60 mA, about 55 mA to about 65 mA, about 60 mA to about 70 mA, about 65 mA to about 75 mA, about 70 mA to about 80 mA, about 75 mA to about 85 mA, about 80 mA to about 90 mA, about 85 mA to about 95 mA, and about 90 mA to about 99 mA, or combinations thereof.

17. The system of claim 14, further comprising a switch operable to electrically connect and disconnect said power source to said conductive element to generate a current pulse rate.

18. The system of claim 17, wherein said current pulse rate occurs in a range of about 1 pulse per second to about 250 pulses per second.

19. The system of claim 18, wherein said switch operable to electrically connect and disconnect said power source to said conductive element to generate a current pulse width.

20. The system of claim 19, wherein said current pulse width of occurs in a range of about 1 millisecond and about 250 milliseconds.

* * * * *